US007598356B2

United States Patent
Bedows et al.

(10) Patent No.: US 7,598,356 B2
(45) Date of Patent: Oct. 6, 2009

(54) METHOD FOR PURIFYING A PROTEIN OF THE CYSTINE-KNOT SUPERFAMILY

(75) Inventors: Elliott Bedows, Bellevue, NE (US); Jason A. Wilken, Omaha, NE (US)

(73) Assignee: Board of Regents of the University of Nebraska by and on Behalf of the University of Nebraska Medical Center, Omaha, NE (US)

( * ) Notice: Subject to any disclaimer, the term of this patent is extended or adjusted under 35 U.S.C. 154(b) by 340 days.

(21) Appl. No.: 10/887,106

(22) Filed: Jul. 8, 2004

(65) Prior Publication Data

US 2006/0009625 A1    Jan. 12, 2006

(51) Int. Cl.
| | |
|---|---|
| A61K 38/00 | (2006.01) |
| C07K 14/435 | (2006.01) |
| C07K 14/475 | (2006.01) |
| C07K 14/48 | (2006.01) |
| C07K 14/49 | (2006.01) |
| C07K 14/495 | (2006.01) |
| C07K 14/51 | (2006.01) |
| C07K 14/54 | (2006.01) |
| C07K 14/575 | (2006.01) |
| C07K 14/745 | (2006.01) |

(52) U.S. Cl. .................. 530/413; 530/300; 530/350; 530/351; 530/380; 530/381; 530/399; 530/412

(58) Field of Classification Search .................. None
See application file for complete search history.

(56) References Cited

U.S. PATENT DOCUMENTS

| 6,121,022 A | 9/2000 | Presta et al. | |
|---|---|---|---|
| 6,414,123 B1 | 7/2002 | Musick et al. | |
| 6,998,253 B1 * | 2/2006 | Presta et al. | 435/69.1 |
| 7,241,593 B2 * | 7/2007 | Fox et al. | 435/69.7 |
| 2002/0146771 A1 | 10/2002 | Burg et al. | |

FOREIGN PATENT DOCUMENTS

| EP | 299746 A1 | 1/1989 |
|---|---|---|
| EP | 1106623 A1 | 6/2001 |
| WO | 88/10269 | 12/1988 |
| WO | WO2004077062 | 9/2004 |
| WO | WO2006078161 | 7/2006 |

OTHER PUBLICATIONS

Marez et al., Biochimie, 69:125-129, 1987.*
Vitt et al., Molecular Endocrinology, 15(5):681-694, 2001.*
Wilken et al., Biochemistry, 43:5109-5118, May 2004.*
Gadkari et al., "Hyperexpression and purification of biologically active human hormone and human chorionic gonadotropin using the methylotropic yeast, *Pichia pastoris*", Protein Expression and Purification 2003 32:175-184.
Kawate et al., "Palmitoylation of Luteinizing Hormone/Human Choriogonadotropin Receptors in Transfected Cells", J. Biol. Chem. 1994 269 (48) : 30651-.
Munshi et al., "Palmitoylation of the luteinizing hormone/human chorionic gonadotropin receptor regultes receptor interaction with the arrestin-mediated in internalization pathway", Eur. J. Biochem. 2001 268:1631-1639.
Reisfeld et al., "Purification of chorionic gonadotropin from the urine of patients with trophoblastic tumors", Biochim. Biophys. Acta 1960 43:540-543.
Zhang et al., "Evidence for monomeric and oligomeric hormone-binding domains in affinity-purified gonadotropin receptor from rat ovary", Proc. Natl. Acad. Sci. 1989 86:8294-8298.
Frietag et al., ""Activated"-Rec A Protein affinity chromatography of LexA repressor and other SOS-regulated proteins", Proc. Natl. Acad. Sci. USA 1989 86:8363-8367.
Recombinant Mouse Noggin/Fc Chimera—Catalog No. 719-NG from R&D Systems, Oct. 19, 2004.

* cited by examiner

*Primary Examiner*—Marianne P Allen
(74) *Attorney, Agent, or Firm*—Senniger Powers LLP

(57) ABSTRACT

The present invention relates to a two-step method for isolating proteins from the cystine-knot superfamily based on dye ligand affinity chromatography and reversed-phase chromatography. Advantageously, the method can be performed in a relatively short period of time, involves inexpensive reagents, and requires little sample preparation before and during the purification process. Protein fusions between cystine-knot proteins and proteins of interest are further provided for the isolation of said protein of interest or complexes containing said protein of interest using the two-step method disclosed.

19 Claims, No Drawings

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial sequence
<220> FEATURE:
<223> OTHER INFORMATION: Cystine-knot consensus sequence
<220> FEATURE:
<221> NAME/KEY: MISC_FEATURE
<222> LOCATION: (2)..(4)
<223> OTHER INFORMATION: "Xaa" represents any amino acid
```

```
<400> SEQUENCE: 1

Cys Xaa Xaa Xaa Cys
1               5
```

METHOD FOR PURIFYING A PROTEIN OF THE CYSTINE-KNOT SUPERFAMILY

This invention was made in the course of research sponsored by the National Cancer Institute (Grant No. P30CA3627). The U.S. government may have certain rights in this invention.

BACKGROUND OF THE INVENTION

The crystal structures of nerve growth factor (NGF), transforming growth factor-beta (TGF-β), platelet-derived growth factor (PDGF), and human chorionic gonadotropin (hCG), from four separate growth factor families revealed that these proteins are structurally related as a superfamily and share a common overall topology (McDonald and Hendrickson (1993) *Cell* 73:421-424). These proteins have little sequence homology, but they all have an unusual arrangement of six cysteines linked to form a "cystine-knot" conformation. One example of a cysteine framework in these proteins consists of four cysteine residues with a cysteine spacing of Cys-Xaa-Xaa-Xaa-Cys (SEQ ID NO:1) and Cys-Xaa-Cys, important for a ring structure formed by eight amino acids. The two additional cysteines form a third disulfide bond that penetrates the ring structure, thus forming the cystine-knot. Other variations of the eight amino acid ring structure include a fourteen- and a sixteen amino acid-ringed cystine-knot that nonetheless, maintains the same overall topology of the superfamily.

The active forms of these cystine-knot proteins are dimers, either homo- or heterodimers (Sun and Davies (1995) *Annu. Rev. Biophys. Biomol. Struct.* 24:269-291). Because of their structure, there appears to be an intrinsic requirement for the cystine-knot proteins to form dimers. This extra level of organization increases the variety of structures built around this simple structural motif (Isaacs (1995) *Curr. Opin. Struct. Biol.* 5:391-395).

The glycoprotein hormone subgroup of cystine-knot proteins are classically considered to be a family of four proteins (chorionic gonadotropin, CG; follicle stimulating hormone, FSH; luteinizing hormone, LH; and thyroid stimulation hormone, TSH) distinguished by the following characteristics. All members of this subgroup are non-covalently associated heterodimers that contain an α-subunit, which is the product of a common gene and a distinct β-subunit, which confers biological specificity (Pierce and Parsons (1981) *Annu. Rev. Biochem.* 50:465-95). Structurally, both the glycoprotein hormone α- and β-subunits each consist of three β-sheets stabilized by hydrogen bonds and a cystine-knot; the subunits align in a head-to-tail manner with the heterodimers being stabilized by a disulfide "seatbelt" (Lapthorn, et al. (1994) *Nature* 369:455-61). Glycoprotein hormones are secreted from either the pituitary (FSH, LH and TSH) or the placenta (CG). Because of their respective roles in human reproduction, FSH, LH and CG are collectively termed gonadotropins.

To study the structure and biological function of cystine-knot proteins, these proteins have been purified using various methods.

Partially purified hCG has been used as starting material (Bahl (1969) *J. Biol. Chem.* 244:567-574; Birken, et al. (1988) *Endocrinology* 123:572-83; Canfield (1971) *Recent Prog. Horm. Res.* 27:121-64; Morgan, et al. (1974) *Endocrinology* 94:1601-6) and, while relatively simple, were only of use for purifying human urinary CG. Purification of gonadotropins from urine or culture media is considerably more complex, and has involved the use of organic or ammonium sulfate precipitation, and hydrophobic interaction chromatography and ion-exchange chromatography (Reisfeld and Hertz (1960) *Biochem. Biophys. Acta* 43:540-3; Gadkari, et al. (2003) *Protein Expr. Purif.* 32:175-84), or antisera (Jiang, et al. (2002) *Mol. Hum. Reprod.* 8:201-12; Manna, et al. (2002) *Hum. Mol. Genet.* 11:301-15). Another purification scheme for CG uses a combination of ammonium sulfate precipitation, hydrophobic interaction chromatography, and ion exchange chromatography (Gadkari, et al. (2003) supra).

Kawate and Menon ((1994) *J. Biol. Chem.* 269:30651-58); Zheng and Menon ((1989) *Proc. Natl. Acad. Sci. USA* 86:8294-8); and Munshi et al. ((2001) *Eur. J. Biochem.* 268: 1631-1639) teach that hCG covalently binds to AFFI-GEL® 10 beads and may be used as a ligand in an affinity column for isolating the LH/hCG receptor.

U.S. Pat. No. 6,414,123 discloses a method for purifying FSH from a sample by applying the sample in a first buffer comprising a pH of less than about 7.5 to a dye affinity chromatography matrix comprising a dye ligand; washing out contaminants from the chromatography matrix with a second buffer comprising a pH of less than about 9.0; and eluting the FSH with a third buffer comprising less than about 0.8 M NaCl and a pH of less than 5.0. An additional purification step is taught which encompasses a hydrophobic solid phase chromatography step.

Needed in the art is a general method for substantially purifying members of the cystine-knot superfamily of proteins that takes advantage of the common structural motif of these proteins. The present invention meets this need in providing a rapid, efficient, two-step method for purifying members of the cystine-knot superfamily.

SUMMARY OF THE INVENTION

The present invention relates to a two-step method for purifying protein members of the cystine-knot superfamily. The method involves the steps of: (a) applying a sample containing a protein of the cystine-knot superfamily to a dye affinity chromatography matrix comprising a dye ligand; (b) removing contaminants from the dye affinity chromatography matrix; (c) eluting the cystine-knot protein from the dye affinity chromatography matrix; (d) applying the eluted cystine-knot protein to a reversed-phase chromatography matrix; (e) removing contaminants from the reversed-phase chromatography matrix; and (f) eluting the cystine-knot protein from the reversed-phase chromatography matrix.

In one embodiment, the protein of the cystine-knot superfamily is a dimer.

In other embodiments, the protein of the cystine-knot superfamily is a platelet-derived growth factor-like protein such as platelet-derived growth factor, vascular endothelial growth factor, or placenta growth factor-1; a transforming growth factor-beta such as a transforming growth factor-beta, a bone morphogenetic protein, or a growth differentiation factor; a neurotrophin such as brain-derived neurotrophic factor/neurotrophin 3, neurotrophin 4, or beta-nerve growth factor; a glycoprotein hormone such as follitropin, lutropin, thyrotropin or chorionic gonadotropin; an interleukin; a coagulogen; a mucin such as mucin-2, mucin-5AC, mucin-6 and von Willebrand factor; a bone morphogenetic protein antagonist such as noggin; or a slit-like protein.

In further embodiments the dye ligand is a triazine dye such as CIBACRON® Blue dye ligand.

In yet other embodiments, the sample is of a physiological pH and the step of removing contaminants from the dye affinity chromatography matrix uses a buffer of a physiological pH.

In a still further embodiment, the step of eluting the cystine-knot protein from the dye affinity chromatography matrix uses a buffer of a physiological pH and a salt concentration of at least 300 mM.

In yet another embodiment, the protein of the cystine-knot superfamily is a fusion protein composed of a protein of the cystine-knot superfamily, or fragment thereof, operably linked with a select protein of interest.

The present invention also relates to a method for purifying a select protein of interest. This method of the invention involves the steps of: (a) obtaining a sample containing a fusion protein comprising a protein of the cystine-knot superfamily, or fragment thereof, operably linked with a select protein of interest; (b) applying said sample to a dye affinity chromatography matrix comprising a dye ligand; (c) removing contaminants from the dye affinity chromatography matrix; (d) eluting the fusion protein from the dye affinity chromatography matrix; (e) applying the eluted fusion protein to a reversed-phase chromatography matrix; (g) removing contaminants from the reversed-phase chromatography matrix; and (h) eluting the fusion protein from the reversed-phase chromatography matrix.

In one embodiment, the method for purifying a select protein of interest further includes the presteps of: (a) preparing a fusion protein comprising a protein of the cystine-knot superfamily, or fragment thereof, operably linked with a select protein of interest; (b) expressing said fusion protein in a host cell; and (c) preparing a sample from said host cell which contains the fusion protein.

In other embodiments, the method for purifying a select protein of interest further includes introducing a protease cleavage site between the protein of the cystine-knot superfamily, or fragment thereof, and the select protein of interest wherein the select protein of interest is isolated by the subsequent step of (i) cleaving the protein of the cystine-knot superfamily, or fragment thereof, from the select protein of interest.

In a still further embodiment, the step of eluting the cystine-knot protein from the dye affinity chromatography matrix uses a buffer of a physiological pH and a salt concentration of at least 300 mM.

The present invention also relates to a method for purifying a select protein of interest operably linked to a cystine-knot tag via a protease cleavage site. This method of the invention involves the steps of: (a) obtaining a first sample containing a fusion protein comprising a protein of the cystine-knot superfamily, or fragment thereof, operably linked with a select protein of interest via a protease cleavage site; (b) applying said first sample to a dye affinity chromatography matrix comprising a dye ligand; (c) removing contaminants from the dye affinity chromatography matrix; and (d) eluting the fusion protein from the dye affinity chromatography matrix using a protease that specifically cleaves the protease cleavage site.

In further embodiments, the dye ligand used in the methods of the invention for purifying a select protein of interest is a triazine dye such as CIBACRON® Blue dye ligand.

In yet other embodiments of the methods for purifying a select protein of interest, the sample is of a physiological pH and the step of removing contaminants from the dye affinity chromatography matrix uses a buffer of a physiological pH.

In other embodiments of the methods for purifying a select protein of interest, the protein of the cystine-knot superfamily is a platelet-derived growth factor-like protein, a transforming growth factor-beta, a neurotrophin, a glycoprotein hormone, an interleukin, a coagulogen, a mucin, or a slit-like protein.

In yet further embodiments, a second sample containing molecules such as, but not limited to, one or more proteins, nucleic acids, or co-factors is applied to a dye affinity chromatography matrix containing a bound select protein of interest so that said one or more proteins, nucleic acids, or cofactors interact with said protein of interest to form a complex, wherein elution of the protein of interest results in the elution of the complex.

A kit for isolating a protein of interest is further provided wherein said kit contains an expression vector encoding a cystine-knot protein tag.

DETAILED DESCRIPTION OF THE INVENTION

The present invention is a simple method for purifying members of the cystine-knot superfamily. The method encompasses two chromatography purification steps which yields a substantially purified preparation of cystine-knot protein. Advantageously, the method can be performed in a relatively short period of time, involves inexpensive reagents, and requires little sample preparation before and during the purification process. Moreover, a cystine-knot protein purified in accordance with the method of the invention comprises both subunits of the dimer.

As used herein, the terms cystine-knot protein, protein containing a cystine-knot, and protein of the cystine-knot superfamily are used interchangeably to refer to the structural class of proteins which contain the art-recognized characteristic six cysteines linked to form a cystine-knot conformation. A protein containing a cystine-knot is intended to include the classically defined members of the cystine-knot superfamily (e.g., nerve growth factor, transforming growth factor-beta, platelet derived growth factor, and human chorionic gonadotropin), as well as the C-terminal cystine-knot family. Such proteins can be purified as monomers or dimers, however, when a functional protein is required it is generally desirable to purify a cystine-knot protein as a dimer. Monomers purified in accordance with the method of the present invention can be used to generate monomer-specific antibodies or can be used in reconstitution experiments with other purified monomers. Fragments of cystine-knot proteins can also be isolated in accordance with the method of the invention, provided that said fragments contain the requisite cysteines necessary to fold into the cystine-knot conformation (i.e., four cysteine residues with a cysteine spacing of Cys-Xaa-Xaa-Xaa-Cys (SEQ ID NO:1) and Cys-Xaa-Cys that form a ring structure and two additional cysteines that form a third disulfide bond which penetrates the ring structure) or overall topography of the cystine knot superfamily of proteins. Said fragments need not be active nor be able to form dimers, however, such characteristics may be desirable depending on intended use the fragment after isolation.

The classically defined members of the cystine-knot superfamily are generally categorized into the families of platelet-derived growth factor-like proteins, transforming growth factor-beta proteins, neurotropins, glycoprotein hormones, interleukins, and coagulogens. See, e.g., The cystine-knot proteins at http://hormone.stanford.edu/.

Platelet-derived growth factor-like proteins include, but are not limited to, PDGFs, vascular endothelial growth factors (VEGF), fallotein, and placenta growth factor-1 (PLGF-1).

In addition to the TGF-$\beta$ proteins (e.g., TGF-$\beta$3, TGF-$\beta$2, TGF-$\beta$1), the bone morphogenetic proteins (BMP) and/or growth differentiation factors (GDF) (Wozney (1992) *Mol. Reprod. Dev.* 32(2):160-7) form a subgroup of the transforming growth factor-beta protein family. Also within this family is the inhibin subgroup (Burger, et al. (1995) *Reprod. Fertil. Dev.* 7(5):997-1002). Specific members of this family include, but are not limited to, BMPs 2-10, mullerian inhibiting factor, glial cell-derived neurotrophic factor (GDNF), activin, persephin, artemin, macrophage inhibitory cytokine-1 (MIC-1), neurturin and the like. Proteins of the TGF-beta family are found in virtually any cell type and throughout the developmental stages of any given species (Sporn, et al. (1986) *Science* 233(4763):532-4).

The neurotropins include, but are not limited to, brain-derived neurotrophic factor/neurotrophin 3 heterodimer, neurotropin 4, neurotropin 3, and β-NGF.

The glycoprotein hormone family includes, but is not limited to, FSH (i.e., follitropin), LH (i.e., lutropin), TSH (i.e., thyrotropin) and CG (i.e., chorionic gonadotropin);

Interleukins include, but are not limited to, interleukin 17F (IL-17F).

Coagulogens include, but are not limited to, coagulogens type I and type II (e.g., from Japanese horseshoe crab).

Members of the C-terminal cystine-knot family are generally categorized into the subgroups of mucin-like proteins and slit-like proteins.

In addition to mucin proteins (e.g., mucin-2, mucin-5AC, mucin-6, and sublingual gland mucin), several additional proteins are in the mucin-like subgroup due to the similarity in the cystine-knot motif. These proteins include, von Willebrand factor (vWF), which acts as a blood clotting agent by propagating agglutination of platelets and their adhesion to the vessel surface (Katsumi, et al. (2000) *J. Biol. Chem.* 275(33):25585-94); Norrie disease protein (NDP); and BMP-antagonists, Cerberus, noggin, TSG, Chordin, USAG-1, SOST, Coco, Gremlin, PRDC and Dan, which antagonize by binding to signaling ligands (Belo, et al. (2000) *Genesis* 26(4):265-70; Piccolo, et al. (1999) *Nature* 397(6721):707-10).

Of the members of the slit-like family, the slit protein plays a vital role in axonal guidance in *Drosophila melanogaster* by acting as a signaling ligand for the robo (roundabout) receptor which leads to a repulsion of axons at the midline (Harris and Holt (1999) *Nature* 398(6727):462-3). Multiple homologs of both slit and robo have been identified in vertebrates and are thought to play similar roles to their fly counterparts in neural development (Brose, et al (1999) *Cell* 96(6):795-806). Slit homologues in the mouse bind robo1 and are expressed within the central nervous system and other developing tissues such as the developing kidney (Yuan, et al. (1999) *Dev. Biol.* 212(2):290-306; (Piper, et al. (2000) *Mech. Dev.* 94(1-2):213-7). Exemplary slit-like proteins include, but are not limited to, human slit-1 and slit-2, and *D. melanogaster* slit.

Cystine-knot proteins can be purified in accordance with the method of the present invention from samples of recombinant or natural origin (e.g., obtained from a mammal such as a human, rat, mouse, cow, dog, cat, monkey, etc.; insect such as *Drosophila melanogastor*; or crustacean such as *Tachypleus tridentatus*). Proteins of recombinant origin can be from expression in bacterial, yeast, insect (e.g., baculoviral), or mammalian expression systems.

Samples that contain cystine-knot proteins can be tissues; bodily fluids such as blood, urine, plasma; culture medium when the protein is secreted in a recombinant system; or cell lysates when the protein is not secreted or excreted. In general, sample preparation prior to the first chromatography step of the method of the present invention can include one or more centrifugation or filtration steps to remove particulate cell debris when present and can further include dilution, concentration, pH adjustment, or adjustment of salinity. For example, it may be necessary to adjust the pH of the sample so that the cystine-knot proteins will bind to the dye ligand in the first chromatography step of the purification method. In accordance with the method of the present invention, the pH of the sample is typically in a pH range of pH 3.0-10.0 or but most suitably in the range of 6.0-8.0. In particular embodiments of the present invention, the sample is at a physiological pH such as 7.4. Methods for preparing protein samples for chromatographic separation are well-known to those of skill in the art. See, e.g., Scopes, et al. (January 1994) In: Protein Purification: Principles and Practice, 3rd edition, Springer Verlag.

The first chromatography step of method of the present invention involves the use of a dye affinity chromatography matrix. A sample containing a protein of the cystine-knot superfamily is applied to a dye affinity column matrix containing a dye ligand. Dye ligands are usually anionic, in which case an anion-exchanger is most appropriate in the method of the invention, but some are cationic, in which case a cation-exchanger is most appropriate. In one embodiment of the purification method of the present invention, the dye ligand is a polysulphonated aromatic ligand such as a triazine dye. In particular embodiments of the present invention, the dye ligand is, for example, CIBACRON® Blue (e.g., 3-GA or F3GA), CIBACRON® Brilliant Yellow 3G-P, Procion Brown MX-5BR, Procion Red H-8BN, Procion Yellow MX-AG, Procion Red HE-3B, Procion Green H-4G, Procion Blue MX-4GD, Procion Red H-3B and Procion Blue MX-R, CIBACRON® brilliant red 3B-A. Other triazine dyes are also suitable and generally known to those of skill in the art of protein biochemistry. In general, any dye ligand having a charge and structure similar to CIBACRON® Blue will be useful in isolating a cystine-knot protein in accordance with the method of the present invention.

The support matrix for the dye ligand is not critical, however, a support matrix based on polysaccharides is generally used (e.g., SEPHAROSE, SEPHADEX, or agarose). The column is equilibrated with buffer at a pH typically ranging from 3.0-10.0, but most suitably in the range of 6.0-8.0. In particular embodiments of the present invention, the column is equilibrated to a physiological pH, such as 7.4.

The sample is applied to the dye affinity chromatography matrix at a salt concentration suitable for allowing binding between the dye ligand and the cystine-knot protein. Binding of the cystine-knot protein to the dye ligand is generally dependent on the pH of the sample and any suitable buffer can be used. However, if an active protein is required, a phosphate or potassium-based buffer may be desirable. Other suitable buffering salts and concentrations thereof for carrying out the dye affinity chromatography step of the invention are generally known in the art of protein purification. After the sample has been applied to the dye affinity chromatography matrix, contaminants (i.e., molecules such as proteins which do not bind to the dye ligand) are removed by washing the column matrix with a buffer, e.g., the buffer used in the preparation of the sample. Subsequent to removing contaminants, the cystine-knot-containing proteins, (also termed cystine-knot proteins) are eluted from the dye affinity chromatography matrix. The concentration of salt (e.g., sodium chloride) for eluting a cystine-knot protein is generally at least 300 mM and can be in the range 300 mM to 3 M or higher depending on the affinity of the cystine-knot protein for the dye ligand. For example, LH can be eluted from a dye ligand with 300 mM, 600 mM, 1500 mM or more NaCl; FSH can be eluted from a dye ligand with 600 mM, 1200 mM, 1500 mM or more NaCl; TSH can be eluted from a dye ligand with 300 mM, 900 mM, 1200 mM or more NaCl; TGF-β can be eluted from a dye ligand with 1500 mM, 2700 mM or more NaCl. Exemplary elution conditions and the resulting fold purification for select proteins of the cystine-knot superfamily are listed in Table 1.

TABLE 1

| Protein | Fraction of maximum recovery/Fold Purification | Fraction of maximum purification/Fold Purification |
|---|---|---|
| hCG[a] | 1200 mM NaCl/161 | 1200 mM NaCl/161 |
| mCG[a] | 600 mM NaCl/12.8 | 900 mM NaCl/13.7 |
| FSH[b] | 1200 mM NaCl/20.7 | 1500 mM NaCl/37.8 |
| LH[b] | 600 mM NaCl/3.0 | 1500 mM NaCl/15.2 |
| TSH[b] | 900 mM NaCl/6.7 | 1200 mM NaCl/8.3 |
| TGF-$\beta_1$[b] | 2700 mM NaCl/43.2 | 2100 mM NaCl/43.8 |
| VEGF[b] | 2100 mM NaCl/26.2 | 2400 mM NaCl/33.8 |
| VWF[b] | * | 1800-2100 mM NaCl |
| Noggin[c] | 2100 mM NaCl/671 | 2100 mM NaCl/671 |

[a]Fold purification determined by activity in a bioassay.
[b]Fold purification determined by ELISA.
[c]Fold purification determined by semi-quantitative enzyme immunoassay.
* Different dilutions of vWF gave varying results by ELISA, making exact assignment difficult. The maximum purification of vWF appeared to occur at 1800-2100 mM NaCl.

While Table 1 discloses the elution conditions and the resulting fold purification of dimers of the cystine-knot superfamily, monomer subunits of cystine-knot-containing dimers have also been shown to bind and be eluted with salt concentrations in the range of 300-900 mM NaCl.

Advantageously, the second chromatography step of method of the present invention can be carried out without manipulating the salt concentration or pH of the protein sample eluted from the dye affinity chromatography matrix. However, it should be understood that such parameters can be modified depending on the reversed-phase chromatography matrix used in the second chromatography step.

In accordance with the method of the invention, the cystine-knot protein sample (i.e., one or more fractions containing the cystine-knot protein) eluted from the dye affinity chromatography matrix is applied to a reversed-phase chromatography matrix that separates proteins based on the principle of partitioning between the mobile and stationary liquid phases. Said step can be carried out by means of either a high-performance liquid chromatography column or a fast protein liquid chromatography column.

In general, the mobile phase encompasses two solvent solutions, a polar and a non-polar solvent, to be blended via a gradient over the course of the chromatographic separation. The polar solvent, designated herein solvent "A", generally contains water and salts. The non-polar solvent, designated herein solvent "B", generally contains water, salts and an organic solvent, such as acetonitrile, methanol, isopropanol or propanol, in an amount ranging from approximately 40-80%.

The cystine-knot protein-containing sample is injected onto a reversed-phase chromatography matrix pre-equilibrated with a mobile phase of the appropriate gradient. The appropriate gradient will vary with a number of factors including the nature of solvents "A" and "B", the salt to be used and the column. Reversed-phase matrices suitable for purification of a cystine-knot protein include columns packed with silica beads bearing alkyl groups ranging in length from 4-18 carbon atoms, i.e., $C_4$-$C_{18}$. Methods for carrying our reversed-phase chromatography are well-established in the art. See, e.g., Scopes, et al. (January 1994) In: Protein Purification: Principles and Practice, 3rd edition, Springer Verlag.

After the cystine-knot protein is applied to the reversed-phase chromatography matrix, contaminants are removed and the cystine-knot protein is eluted. Elution can be carried using a continuous gradient or using a step gradient of one or more buffers with varying amounts of organic solvent.

By way of illustration, proteins from various families of the cystine-knot superfamily were purified in accordance with the method of the present invention. It was found that the method of the present invention can be used to isolate to homogeneity any protein having the requisite cysteines necessary to fold into the cystine-knot conformation (Table 3).

Using a series of well-known mutants of GPH-α and CG-β, the binding interaction between a cystine-knot protein and a triazine dye ligand was analyzed. 293T cells were transiently transfected with plasmids encoding the GPH-α and CG-β subunits listed in Table 2 and were metabolically labeled with [$^{35}$S]-cysteine. Radiolabeled subunits were subsequently purified by immunoprecipitation and reversed-phase HPLC using standard methods (Wilken and Bedows (2004) Biochemistry 43(17) 5109-5118). The purified subunits were then mixed with ULTRACULTURE™, and applied to AFFI-GEL® Blue Gel columns as disclosed herein. The subunits were then eluted with increasing concentrations of NaCl. As shown in Table 2, each of the subunits was bound to the CIBACRON® Blue dye ligand and was eluted with increasing NaCl. GPH-α or hCG-β alone bound CIBACRON® Blue dye ligand, indicating that an intact heterodimer was not required for binding to CIBACRON® Blue dye ligand.

TABLE 2

| Subunit name | Effect of modification | Fraction of maximum recovery |
|---|---|---|
| GPH-α WT | none | 300 mM NaCl |
| hCG-β WT | none | 600 mM NaCl |
| $\alpha_{7-31/57-87}$ | Elimination of cystine-knot | 300 mM NaCl |
| $\alpha_{knot}$ | Elimination of non-cystine-knot disulfides | 300 mM NaCl |
| $\alpha_{Loop2Gly}$ | Replace L2 loop with Gly residues | 300 mM NaCl |
| α-Trypsin | Removal of L3 loop, multiple backbone breaks | Sample failed to bind |
| β-Trypsin | Multiple backbone breaks | 300 mM NaCl |

To further investigate the binding interaction between the cystine-knot protein and dye ligand, two genetically altered GPH-α mutants were utilized, $\alpha_{7-31/59}$-87, lacking the cysteine residues required for α-subunit cystine-knot formation and $\alpha_{knot}$ lacking all of the α-subunit cysteine residues except those required for cystine-knot formation (Darling, et al. (2001) Biochemistry 40:577-85). Both mutants were tested for their respective abilities to be purified in accordance with the method of the present invention. It was found that both mutant subunits bound to CIBACRON® Blue dye ligand, therefore none of the cysteine residues were necessary or sufficient for binding to CIBACRON® Blue dye ligand. Another GPH-α mutant, $\alpha_{Loop2Gly}$, having a run of 20 glycine residues in place of the L2 loop (Darling, et al. (2001) supra), also bound to CIBACRON® Blue dye ligand. Thus, the L2 loop appears to be dispensable for binding to CIBACRON® Blue dye ligand.

To determine whether the hydrophobic interface between the L1 and L3 loops of a glycoprotein hormone were involved in binding to CIBACRON® Blue dye ligand, radiolabeled wild-type GPH-α and hCG-β were treated with trypsin and binding to CIBACRON® Blue dye ligand was determined. Treatment with trypsin removed the L3 loop from GPH-α, but did not remove L3 from hCG-β due to the stabilizing effect of disulfide 23-72 that bridges hCG-β L1 and L3. Trypsin-treated GPH-α did not bind to CIBACRON® Blue dye ligand, whereas trypsin-treated hCG-β did bind CIBA-CRON® Blue dye ligand, indicating that the L1 and L3 interface is the binding site for CIBACRON® Blue dye ligand.

It is contemplated that the method of the present invention is useful for purifying cystine-knot proteins used for commercial, research, and pharmaceutical purposes. Further, the method of the present invention is useful for purifying a fusion protein composed of a protein of the cystine-knot superfamily, or fragment thereof, operably linked with a select protein of interest.

Given the ease of cystine-knot protein isolation afforded by the method of the present, the present invention further relates to the use of cystine-knot proteins, or fragments thereof which bind to an affinity dye ligand, as protein tags for the isolation of select proteins of interest. While the entire sequence of a cystine-knot protein monomer can be fused to the protein of interest, a fragment of a cystine-knot protein can also be used so long as the fragment meets the criteria of containing the requisite cysteines necessary to fold into the cystine-knot conformation and bind to an affinity dye ligand. Therefore, as used hereafter, a cystine-knot protein tag is intended to include full-length cystine-knot protein sequences as well as fragments thereof.

As it has been demonstrated that the various cystine-knot proteins bind with varying affinity to a dye ligand, it is contemplated that select cystine-knot proteins will be useful depending on the desired purity of the protein of interest. For example, when a protein for which a high level of purity is desired (e.g., for therapeutic applications) it is advantageous to use a cystine-knot protein which has a high affinity for the dye ligand (i.e. elutes from the dye ligand under high salt conditions). Alternatively, when protein complexes are desired, it is advantageous to use lower salt concentrations for protein elution, so that binding of the complex subunits is not disrupted. In the former case, cystine-knot protein tags such as TGF-β are useful; in the latter case, cystine-knot protein tags such as hCG-β are useful. It is contemplated that, without limitation, any protein can be tagged using a cystine-knot protein tag.

Molecular tools and methods for the generation and expression of fusion proteins are well-known to those of skill in the art. See, e.g., Sambrook and Russell, Molecular Cloning: A Laboratory Manual, 3$^{rd}$ Edition, Cold Spring Harbor Laboratory Press, Cold Spring Harbor, N.Y. or Ausubel, et al. Short Protocols In Molecular Biology, 4$^{th}$ Edition, 1999, Wiley John and Sons, Inc.

In general, the cystine-knot protein is operably linked to the protein of interest either directly or via a linker (e.g., a protease cleavage site) so that when transcribed and translated, the cystine-knot protein and protein of interest are one contiguous protein sequence. Accordingly, such a fusion protein is prepared by ligating the nucleic acid sequence encoding for the cystine-knot protein tag to either the 5' or 3' end of the nucleic acid sequence encoding a protein of interest (i.e., to generate an N-terminal or C-terminal fusion, respectively), so that that tag is translated in-frame with the protein of interest. Subsequently, the ligated nucleic acid sequence encoding the fusion protein is incorporated into a recombinant expression vector in a form suitable for expression of the fusion protein in a host cell. A suitable form for expression provides that the recombinant expression vector includes one or more regulatory sequences operably linked to the nucleic acids encoding the fusion protein in a manner which allows for transcription of the nucleic acids into mRNA and translation of the mRNA into the fusion protein. Regulatory sequences may include promoters, enhancers and other expression control elements (e.g., polyadenylation signals). Such regulatory sequences are known to those skilled in the art and are described in Goeddel, Gene Expression Technology: Methods in Enzymology 185, Academic Press, San Diego, Calif. (1990). It should be understood that the design of the expression vector may depend on such factors as the choice of the host cell to be transfected and/or the level of gene expression required. It is contemplated that nucleic acid sequences encoding the cystine-knot tag can be incorporated into an expression vector preceded or followed by a multiple cloning site for easy insertion of nucleic acid sequences encoding a protein of interest. Numerous host cells can be selected as appropriate for transformation and expression of the described fusion proteins, including mammalian, insect, fungal, plant and bacterial host cells which are particularly desirable. Commonly used bacterial strains include *Escherichia*, *Klebsiella*, *Erwinia*, *Bacillus*, *Staphylococcus* and *Salmonella*. *E. coli* TG-1, or *E. coli* BL-21 are well-known bacterial strains for protein expression. Eukaryotic cells such as *Saccharomyces cerevisiae*, *Shizosaccharomyces pombe*, *Pichia* sp., *Neurospora*, transgenic plants (e.g., tobacco, maize, or potato), insect cells (e.g., Sf9 and Sf21) and mammalian cell lines can also be employed with good results.

The recombinant DNA of the present invention can be used either in the form of an expression vector or as the DNA alone to transform a host cell. Methods of injecting DNA directly into a cell are known, such as by electroporation, biolistic techniques or transformation. Alternatively, vectors incorporating the DNA can be prepared, for example, by packaging in vitro into bacteriophage as found in Sambrook, et al. supra. Cells are then infected with the recombinant phage, plated and grown in appropriate media.

Vectors employed in prokaryotic systems will include an origin of replication, a promoter and transcriptional termination signal and preferably a selective marker. Examples of promoters include tac, T7, trc, trp, or $P_L$. Some promoters such as Ptac or Ptrc, when present in *E. coli* host cells, are repressed by lac repressor. Expression of the recombinant protein encoded in the vector can be induced with IPTG. Other inducible promoters include Pmal and the aforementioned trp and $P_L$. This feature is useful for expression of toxic proteins because one can increase cell density in the culture prior to inducing expression of the desired polypeptide.

Regarding eukaryotic cells, it is contemplated that numerous eukaryotic expression vectors could be utilized for the expression of fusion proteins that incorporate cystine-knot protein tags, whether wild-type or mutant; for example, Baculovirus-based, glutamine synthetase-based, neomycin phosphotransferase or dihydrofolate reductase-based systems can be employed. Plasmid vectors incorporating an origin of replication and an efficient eukaryotic promoter, as exemplified by the eukaryotic vectors of the PCNV series, such as PCNV-5, can also be of use. Other suitable vectors for use in prokaryotic or eukaryotic expression systems are well-known in the art and many are commercially available.

For protein expression, the coding sequence is positioned adjacent to and under the control of the promoter. It is understood in the art that to bring the coding sequence under the control of such a promoter, the transcriptional reading frame of the fusion protein is positioned between about 1 and 50 nucleotides downstream of (i.e., 3' of) the selected promoter.

In eukaryotic systems, it is also typically desirable to incorporate an appropriate adenylation site (e.g., 5' AATAAA-3') in the most 3' segment of the transcript if not contained within either the nucleic acid sequence encoding the protein of interest or cystine-knot protein. Typically, the poly A addition site is placed about 30 to 2000 nucleotides downstream of the termination site of the protein at a position adjacent to a transcription termination signal.

Once the expression vector encoding for the fusion protein is generated, it can be introduced into an appropriate host cell using standard methods such as transfection, electroporation, biolistic transformation, *Agrobacterium*-mediated transformation, and the like. After growing the transformed host cell for a suitable amount of time to express the fusion protein, the host cell is generally lysed to release the fusion protein. The fusion protein sample is then isolated in accordance with the two-step chromatographic method disclosed herein.

Alternatively, a signal sequence can be introduced into the fusion protein so that the fusion protein is secreted into the medium. A signal sequence can be the endogenous signal sequence present in the protein of interest or can be a component of the vector and should be one that is recognized and processed (i.e., cleaved by a signal peptidase) by the host cell. For production in a prokaryote, a prokaryotic signal sequence from, for example, alkaline phosphatase, penicillinase, outer membrane lipoprotein (lpp), or heat-stable enterotoxin II leaders can be used. For yeast secretion, one can use, e.g., the yeast invertase, alpha factor, or acid phosphatase leaders, the *Candida albicans* glucoamylase leader (EP 362,179), or the like (see, for example WO 90/13646). In mammalian cell expression, signal sequences from secreted polypeptides of the same or related species, as well as viral secretory leaders, for example, the herpes simplex glycoprotein D signal can be used. Accordingly, the fusion protein sample is obtained by removing the cellular debris and isolating the fusion protein from the medium using the two-step chromatographic method disclosed herein.

The inclusion of cleavable linker sequences or protease cleavage site such as those specific for Factor XA, enterokinase (INVITROGEN™, San Diego, Calif.), uPA, thrombospondin, or matrix metalloprotease between the cystine-knot protein tag and the protein of interest can be used to further facilitate purification of the protein of interest. In one embodiment, the fusion protein contains a protease cleavage site located between the cystine-knot tag and the protein of interest, said fusion protein is eluted from the reversed-phase matrix and the protein of interest is subsequently cleaved from the cystine-knot tag using a protease that specifically recognizes the protease cleavage site. In another embodiment, the fusion protein containing a protease cleavage site located between the cystine-knot tag and the protein of interest is eluted from the dye affinity matrix, cleaved with a protease that specifically recognizes the protease cleavage site and the protein of interest is further purified if desired (e.g., by reversed-phase chromatography to remove the protease, the cystine-knot tag, and salts). In an alternate embodiment, the fusion protein containing a protease cleavage site located between the cystine-knot tag is applied to an affinity dye ligand matrix, the column is washed to remove contaminants, and the protein of interest is directly eluted from said matrix using a protease that specifically recognizes the protease cleavage site thereby separating the protein of interest from the cystine-knot tag that remains bound to the affinity dye ligand.

The present invention further provides a kit for tagging a protein of interest. A kit of the invention comprises a first container means containing an expression vector harboring nucleic acid sequences encoding a cystine-knot protein, or fragment thereof. For ease of inserting nucleic acid sequences encoding a protein of interest, the expression vector can further contain a multiple cloning site (i.e., a nucleic acid sequence having one or more sequences that are specifically recognized and cleaved by one or more restriction enzymes) located either 5' or 3' (i.e., upstream or downstream, respectively) of the nucleic acid sequences encoding the cystine-knot protein tag. As will be understood by one of skill in the art, insertion of nucleic acid sequences encoding a protein of interest will result in an in-frame fusion between the protein of interest and the cystine-knot tag at either the N- or C-terminus of the protein of interest. Moreover, the expression vector can encode for a protease-sensitive linker that is translated in-frame between the protein of interest and the cystine-knot protein. The kit can also contain other solutions necessary or convenient for cloning nucleic acid sequences encoding a protein of interest into the expression vector of the kit. The container can be made of glass, plastic or foil and can be a vial, bottle, pouch, tube, bag, etc. The kit may also contain written information, such as procedures for carrying out the present invention or analytical information, such as the amount of reagent contained in the first container means. The container can be in another container, e.g., a box or a bag, along with the written information.

A cystine-knot tagged protein and method for isolating the same can be used, for example, to identify novel protein-protein complexes. In this example, nucleic acid sequences encoding a fusion protein consisting of a cystine-knot tag operably linked or fused to a novel protein of unknown function (i.e., the bait protein) via a protease-sensitive linker are cloned into an expression vector and transformed into a host cell for recombinant protein expression. Culture media containing the secreted recombinant fusion protein is collected and applied to an affinity dye ligand matrix and washed with low salt buffer to remove non-specific interactions (i.e., washed until the absorbance reaches baseline). Subsequently, a second sample (e.g., a cell lysate, a blood product, or other bodily fluid) is applied to the dye ligand matrix containing the bound fusion protein to allow for protein-protein interactions to occur between the bait protein and proteins of the sample. Non-specific factors are removed by washing the dye ligand matrix. Buffer containing a protease that specifically cleaves the protease-sensitive linker between the bait and the cystine-knot tag is then applied to the dye ligand matrix to release the novel protein-protein complex formed between the bait protein and the sample proteins. The protease and the novel protein-protein complex that contains the bait and one or more additional proteins are subsequently eluted from the matrix. Advantageously, the bait protein does not need to be purified before being applied to the affinity dye ligand matrix and this method can be used for rapid screening of protein complexes of a series of proteins (e.g., a panel of mutant proteins).

As a further example, a cystine-knot tag can be used to identify transcription factor-DNA complexes. In this example, a transcription factor is the bait protein that is fused to the cystine-knot tag via a protease-sensitive linker. A first sample containing the resulting fusion protein is applied to a dye ligand matrix and washed. Subsequently, a second sample containing a nucleic acid (e.g., sheared genomic DNA, cloned promoter or promoter fragments, or oligonucleotides) is applied to the matrix. After additional washing to remove non-specific binding, the nucleic acid/transcription factor complex is eluted by applying to the matrix a protease that specifically cleaves the protease sensitive linker.

Moreover, a cystine-knot tag can be used to identify protein co-factors. In this example, the cystine-knot tag is fused to a bait protein that requires a previously unidentified co-factor. A first sample containing the resulting fusion protein is applied to the dye ligand matrix, a second sample containing a cocktail of co-factors (e.g., NADH, inositol, and the like) is then applied to allow binding between the co-factor and the bait protein, and the bait protein/co-factor complex is released by protease digestion of the linker located between the bait protein and the cystine-knot tag.

It is contemplated that the method of the invention can be used in a high-throughput 96-well format for screening a large number of bait proteins and/or samples to identify complexes with techniques such as mass spectroscopy. While proteins, nucleic acids and co-factors have been specifically disclosed herein, it is contemplated that any molecule such as a drug (e.g., heterocyclic compound, cyclic peptide, etc), lipid, carbohydrate, and the like can be bound to the protein of interest, form a complex, and be isolated as a complex using the methods disclosed herein.

The invention is described in greater detail by the following non-limiting examples.

EXAMPLE 1

Materials and Methods

Cell Culture. Chinese Hamster Ovary (CHO) cells stably expressing wild-type glycoprotein hormone-α and either human (h)CG-β or macaque (m)CG-β (Wilken and Bedows (2004) supra) were seeded into FALCON™ roller bottles and maintained with ULTRACULTURE™ (BioWhittaker, Walkersville, Md.) supplemented with penicillin/streptomycin (100 units/mL and 100 µg/mL, respectively) (INVITROGEN™, Carlsbad, Calif.), and 250 µg/mL G418 (INVITROGEN™) for hCG-β and 50 µM methionine sulfoximine (MSX; Sigma, St. Louis, Mo.) for mCG-α. Human embryonic kidney (HEK) cells stably transfected with the human LH/CG receptor (HEK LH/CG-R cells) were cultured in low-glucose Dulbecco's Minimal Essential Medium (DMEM; INVITROGEN™) containing penicillin/streptomycin as above, 2 mM glutamine and 5% heat-inactivated fetal bovine serum (INVITROGEN™). For CG bioassays, HEK LH/CG-R cells were seeded in the above media supplemented with 0.5 mg/ML geneticin (INVITROGEN™). 293T cells were grown in high-glucose DMEM supplemented with penicillin/streptomycin and 10% fetal bovine serum (Atlanta Biologicals, Inc., Norcross, Ga.).

Affinity Chromatography. AFFI-GEL® Blue Gel agarose (CIBACRON® Blue F3GA dye ligand; BIO-RAD®, Hercules, Calif.) was packed into columns equilibrated with at least five column volumes of 10 mM sodium phosphate, pH 7.4 (Buffer A). Conditioned culture media containing secreted glycoprotein hormone analogs were applied to the column and eluted by gravity filtration and eluted with Buffer A at varying concentrations of NaCl. Samples were collected in either 4 mL or 10 mL fractions and analyzed for protein content and protein gonadotropin content by one of the appropriate assays disclosed herein.

Preparation of Samples for Purification. Media containing the desired protein(s) from CHO cells maintained in ULTRACULTURE™ was clarified by centrifugation for 30 minutes at 2000×g. Tris-HCl (2 M, pH 8.0) was added dropwise to adjust conditioned media to pH 7.4. FSH (25 IU; GONAL-F™, Serono, Rockland, Mass.; FOLLISTIM®, Organon, West Orange, N.J.) was added to 1 mL of ULTRACULTURE™, and diluted to 10 mL with Buffer A. TSH (5 µg, 7 IU/mg, Sigma), LH (5 µg, 11000 IU/mg, Sigma), both isolated from human pituitary, or 20 ng of TGF-β were dissolved in 1 mL of ULTRACULTURE™ and diluted to 10 mL with Buffer A, pH 7.4.

Determination of Protein Content. Sample fractions (200 µL) and blanks were routinely added to a 96-well UV-permissive plate (Costar) and absorbance at 280 nm was measured on a SPECTRAMAX® plate reader. For analytical purposes, 25 µL sample fractions were assayed by the bicinchronic acid method (BCA; Pierce, Rockland, Ill.). Bovine serum albumin solutions were used as standards.

Measurement of CG Concentration. Human CG and macaque CG were assayed by a luminescence LH/CG bioassay (Jia, et al. (1993) Biol. Reprod. 49:1310-6). Briefly, immortalized HEK cells stably transfected with LG/CG receptor and a cAMP-responsive luciferase reporter were seeded into 96-well plates containing growth media. Experimental samples or recombinant hCG standard (Sigma) were incubated 18 hours. Cells were lysed with 100 µL lysis buffer as per manufacture's instructions (PROMEGA®, Madison, Wis.) and incubated with shaking at 22° C. for 30 minutes. Lysate aliquots (25 µL) were mixed with 100 µL luciferase assay reagent (PROMEGA®), and chemiluminescence measured by TOPCOUNT® (Packard Instrument Co, Meriden, Conn.).

Measurement of LH, FSH, TSH and TGF-β Concentrations. LH, FSH, and TSH concentrations were assayed by ELISA (MP Biomedicals, Orangeburg, N.Y.). TGF-β concentration was also assayed by ELISA (BD PharMingen, San Diego, Calif.). All LH, FSH, TSH, and TGF-β samples purified by AFFI-GEL® Blue Gel were assayed at 1:5 or 1:10 concentration so that the activity could be assayed in the linear range. Acetonitrile did not interfere with any of the above assays tested.

Reversed-phase HPLC Purification. Fractions eluted from CIBACRON® Blue dye ligand were injected onto a VYDAC® 300-Å $C_4$ reversed-phase column equilibrated with 90% Buffer A and 10% Buffer B (50% acetonitrile/10 mM sodium phosphate, pH 7.4). After the total volume of all fractions was injected, proteins were eluted from the column using the following acetonitrile gradient: isocratic 5% acetonitrile for 20 minutes followed by 1% acetonitrile/minute for 20 minutes and 0.21% acetonitrile/minute for 120 minutes. The flow rate was 1 mL/minute. Fractions were collected in 4 minute intervals and analyzed for bioactivity and protein content.

SDS-PAGE Analysis. Samples were diluted with an equal volume of 125 mM Tris-HCl (pH 6.8) containing 2% SDS, 20% glycerol and 40 µg/mL bromophenol blue. Samples were loaded on polyacrylamide gradient slab gels (5-20%) and proteins were separated using standard methods (Laemmli (1970) Nature 227:680-5). After the dye front had reached the bottom of the gel, the gel was rinsed and stained with BIO-SAFE™ COOMASSIE® (BIO-RAD®) as per manufacturer's instructions.

Preparation and Purification of Radiolabeled CG Subunits. 293T cells ($2\times10^6$) were plated into 60-mm plastic dishes and grown to 70-80% confluency overnight. Plasmid DNA was precipitated using standard methods (Darling, et al. (2000) J. Biol. Chem. 275:15413-21). To ensure uniform precipitation, one large-scale preparation was distributed equally among dishes. Cells were incubated for 2 days at 37° C. prior to metabolic labeling. Transiently transfected 293T cells were pulse-labeled for 30 minutes with L-[$^{35}$S]Cysteine (~1100 Ci/mmol; PerkinElmer Life Sciences, Boston, Mass.; 50-150 µCi/mL) in serum-free medium lacking cysteine (Bedows, et al. (1993) J. Biol. Chem. 268:11655-62). Pulse incubations were carried out using standard methods (Wilken and Bedows (2004) supra) and cells were chased overnight with complete media. Chase media were saved for analysis of CG-β secreted subunits. Immunoreactive forms of hCG-β and mCG-β were precipitated with polyclonal antiserum that recognizes all known conformations of hCG-β (Beebe, et al. (1990) J. Biol. Chem. 265:312-7). Immunoprecipitations were carried out at 4° C. overnight with rotation in the dark. Immune complexes were precipitated with protein A-SEPHAROSE® (Sigma) and prepared using well-established methods (Bedows, et al. (1992) *J. Biol. Chem.* 267: 8880-6).

EXAMPLE 2

Purification of CG

CHO cells stably expressing hCG or mCG were cultured in roller bottles. Aliquots of media containing secreted gonadotropin were routinely assayed for their protein content by BCA analysis or absorbance at 280 nm and for bioactivity using the HEK-luciferase bioassay disclosed herein. Table 3 lists the measured bioactivity of media samples for hCG (15 IU/mL) and mCG (32 IU/mL), and the specific activities of hCG and mCG samples calculated in IU/mg protein.

TABLE 3

| Purification Step | CG conc. (IU/mL) | Protein Content (mg/mL) | Specific Activity (IU/mg) | CG Yield (IU) | Recovery (%)/Purification factor |
|---|---|---|---|---|---|
| (A) hCG media | 15 | 3.62 | 4.14 | 1500 | 100/1 |
| $^a$AFFI-GEL® Blue agarose | 9.4 | 0.054 | 42 | 1129 | 75.3/126 |
| $^b$RP-HPLC | 8.13 | 0.007 | 1233 | 293 | 19.5/298 |
| (B) mCG media | 32.2 | 3.59 | 8.97 | 3220 | 100/1 |
| $^c$AFFI-GEL® Blue agarose | 113.5 | 1.65 | 68.8 | 3177 | 99/8.7 |
| $^d$RP-HPLC | 85.2 | .012 | 7100 | 1701 | 52.8/792 |

Pooled eluent fractios were assayed, $^a$fractions 11-40, $^b$fractions 28-36, $^c$fractions 5 and 7-12, and $^d$fractions 17-21.

For purification, conditioned media was diluted to 10 mL with Buffer A and applied to a column containing 1 mL of AFFI-GEL® Blue Gel. The flow-through was monitored for protein content and hCG bioactivity and revealed that no CG was detectable, indicating that like albumin and several other proteins, hCG bound to the column. The AFFI-GEL® Blue Gel column was then washed with 10 column volumes of Buffer A containing increasing concentrations of NaCl. At each step, protein content and CG bioactivity was determined. Bioactivity of hCG was first detected in the 600 mM NaCl wash, with maximum activity in the 1200 mM NaCl wash. The 1200 mM fraction also had the greatest specific activity (309 IU/mg protein), representing approximately a 160-fold purification.

This purification method was repeated with the conditioned media of CHO cells expressing mCG. Like hCG, mCG bound to the AFFI-GEL® Blue Gel column in Buffer A. But mCG bioactivity was first detected in the 300 mM NaCl wash. The maximum bioactivity was found in the 600 mM NaCl wash while the 900 mM NaCl wash had the greatest specific activity (23 IU/mg protein), which represented a 14-fold purification.

CG binding capacity of CIBACRON® Blue ligand was analyzed using the following assay. Media, diluted 1:3 in Buffer A was allowed to flow through columns packed with 1 mL of AFFI-GEL® Blue resin. Four mL fractions were collected and assayed for bioactivity as described herein. Bioactivity of hCG was not detectable until fraction 20, indicating that 1 mL of AFFI-GEL® Blue Gel was capable of binding the CG of 19 mL of media with hCG at 15 IU/mL, or ~285 IU hCG. By contrast, mCG bioactivity was detected in fraction 4, indicating that 1 mL of AFFI-GEL® Blue Gel was capable of binding the CG of 3 mL of media with mCG at 32 IU/mL, or ~96 IU mCG. Thus, CIBACRON® Blue ligand had greater affinity for hCG than mCG as measured by binding capacity and ionic strength necessary for dissociation.

CIBACRON® Blue ligand bound both hCG and mCG at NaCl at ionic strengths of 140 mM (physiological). Therefore, media adjusted to pH 7.4 was directly applied to the AFFI-GEL® Blue Gel column. Columns packed with either 6 mL or 20 mL of AFFI-GEL® Blue Gel resin were prepared for large scale purification of 100 mL of hCG and mCG from the conditioned media of CHO cells expressing these hormones, respectively. Columns were washed with 100 mL of Buffer A containing 200 mM NaCl and CG was eluted by applying 200 mL of Buffer A containing 2 M NaCl to the columns. Human or monkey CG was recovered only in the 2 M NaCl fractions while the vast majority of total protein was recovered in the media sample effluent and the 200 mM NaCl wash.

CIBACRON® Blue ligand provided partially purified preparations of both hCG and mCG; however, the purified CG's were recovered in fairly large volumes with high NaCl concentrations. It was noted that CG could be eluted from a $C_4$ reversed phase-HPLC (RP-HPLC) column using an acetonitrile gradient of 0-50% containing 10 mM phosphate buffer, pH 7.4. Advantageously, this additional purification of CG via RP-HPLC would provide that the injected sample is desalted and eluted in a low ionic-strength buffer at physiological pH that is suitable for concentration under vacuum. Accordingly, pooled fractions containing hCG or mCG eluted from CIBACRON® Blue ligand columns were injected onto a $C_4$ reversed phase column and eluted with an acetonitrile gradient in 10 mM phosphate, pH 7.4. Human CG was recovered between 40-50% acetonitrile, while macaque CG was recovered between 30-44% acetonitrile. Human CG fractions 28-36 and macaque CG fractions 17-21 had the greatest specific activity and were pooled and concentrated to 1 mL each under vacuum. The pooled samples had specific activities of 1233 and 7100 IU/mg, a 298- and 792-fold purification over the media sample, and a 29- and 103-fold purification over CG eluted from the CIBACRON® Blue ligand column, respectively.

To verify the purity of mCG, aliquots of mCG from conditioned CHO cell culture media, CIBACRON® Blue ligand purification, and RP-HPLC purification steps were analyzed by SDS-PAGE stained with COOMASSIE® blue. Macaque CG was not detectable as a clear band in cell culture media, but was clearly enriched in the CIBACRON® Blue ligand-purified fraction. Bands corresponding to mCG-β subunit, mCG dimer, and a fainter albumin band were the only bands clearly visible in the lane containing HPLC purified mCG.

EXAMPLE 3

Purification of Other Glycoprotein Hormones

There are four naturally occurring glycoprotein hormones that share a common alpha subunit. Of these LH shares a common receptor with CG, the LH/CG receptor. X-ray structures of CG and FSH have been determined (Lapthorn, et al. (1994) supra; Fox, et al. (2001) *Mol. Endocrinol.* 15:378-89) and demonstrate that these two hormones share a common overall 3-dimensional structure although their amino acid sequences vary extensively. Accordingly, each glycoprotein hormone family member was purified using the same methodology that proved successful for hCG and mCG purification. Human LH (5 µg; Sigma) was dissolved in 1 mL of ULTRACULTURE™ diluted to 10 mL to reduce ionic strength and applied to a 1 mL AFFI-GEL® Blue Gel column. Flow-through was collected and Buffer A containing increasing concentrations of NaCl was passed through the column as described herein. The effluents were each analyzed by absorbance at 280 nm and LH ELISA. LH began to elute at 300 mM NaCl, with maximum activity at 600 mM NaCl, while maximum specific activity was obtained with a 1500 mM NaCl elution (~65-fold purification).

FSH was purified using 25 IU of FSH (GONAL-F™, Serono; FOLLISTIM®, Organon). FSH began to elute at 600 mM NaCl, with a maximum activity at 1200 mM NaCl elution, while maximum specific activity was obtained with a 1500 mM elution (~40-fold purification).

Similarly, human TSH (5 µg) was purified. TSH began to elute at 300 mM NaCl, with a maximum activity at 900 mM NaCl, and maximum specific activity obtained with a 1200 mM NaCl elution (~10-fold purification).

In the second step of the purification method of the invention, the glycoprotein hormones were purified by RP-HPLC with 10 mM phosphate, pH 7.4, using the entire 10 mL fraction of CIBACRON® Blue ligand-purified hormone with the highest concentration of hormone activity (600 mM NaCl LH fraction, 1200 mM NaCl FSH fraction, and 900 mM NaCl TSH fraction; see Table 1). Because of the very low protein concentration of the RP-HPLC fractions, a BCA protein assay was used in addition to $A_{280}$ to determine protein amounts. In control experiments, BSA could be detected at a lower limit of ~1 µg/mL by the BCA method. Therefore, the upper limit of protein concentration of samples whose absorbance at 526 nm by the BCA method was below the detection limit of 1 µg/mL was defined as 1 µg/mL. LH eluted mostly between fractions 14-33 (26-44% acetonitrile). Fraction 23 had the highest LH concentration 105 mIU/mL. Because the protein concentration of this fraction, concentrated from 4 mL to 1 mL, was less than the detection limit for the BCA assay, the protein concentration of this fraction was set at approximately 250 ng/mL; therefore, the specific activity of fraction 23 was approximately 420 IU/mg, a >70 fold total purification.

FSH eluted mostly in fractions 10 and 11 (~25% acetonitrile) of RP-HPLC. Fraction 10 had an FSH concentration at 460 mIU/mL. Since the protein content of fraction 10, concentrated from 4 mL to 1 mL, was below the 1 µg/mL detection limit of the BCA assay, the protein concentration was set at approximately 250 ng/mL. Therefore, the specific activity of fraction 10 of FSH was approximately 1.84 IU/mL, a >1300-fold total purification.

When TSH was purified by RP-HPLC it eluted between fractions 12 and 27 (26-38% acetonitrile). Fraction 15 had the highest TSH concentration at 240 pIU/mL. The protein content of this fraction, concentrated from 4 mL to 1 mL, was also less than the detection limit of 1 µg/mL. Therefore, the protein concentration for TSH was set at 250 ng/mL and its specific activity was approximately 960 IU/mg, representing a >320-fold total purification.

EXAMPLE 4

Purification of TGF-β

TGF-β has a similar structure to the members of the glycoprotein hormone family, in that it is a dimer in which each subunit contains a cystine-knot and three hairpin β-sheet loops (Lapthorn, (1994), supra). Therefore, the method of the present invention was used in the purification of TGF-β. TGF-β (20 ng) was diluted into 1 mL of ULTRACULTURE™ and 9 mL of Buffer A, applied to a 1 mL CIBACRON® Blue ligand, and eluted stepwise with increasing NaCl concentrations. It was found that TGF-β had a very strong affinity for the CIBACRON® Blue ligand. TGF-β was not detected until the 1500 mM NaCl wash, with maximum purification at 2700 mM NaCl. Although TGF-β did not efficiently bind to a $C_4$ reversed-phase column under the conditions disclosed herein, an overall purification of >100-fold was obtained for TGF-β using the method of the invention.

EXAMPLE 5

Purification of Other Cystine-Knot Proteins and a Fusion Protein Thereof

Using the method disclosed herein, members of other families of the cystine-knot superfamily were purified. Samples of VEGF (R&D Systems, Minneapolis, Minn.) and vWF (EMD Biosciences, Darmstadt, Germany) were prepared and isolated using the two-step method described herein resulting in a >25-fold overall purification of VEGF (see Table 1).

Further, a recombinant mouse noggin protein fused to the Fc region of human IgG via a short linker domain (Catalog No. 719-NG, R&D Systems, Inc., Minneapolis, Minn.) was purified 670-fold using the method disclosed herein. Further, it was demonstrated that noggin and Fc were co-purified as the fractions containing high levels of noggin relative specific activity also contained high levels of Fc relative specific activity. These data demonstrate that a cystine-knot tag (e.g., noggin) can be used in the purification of a protein of interest (e.g., human Fc).

What is claimed is:

1. A method for purifying a protein of the cystine-knot superfamily comprising:
    (a) applying a sample containing a protein of the cystine-knot superfamily to a dye affinity chromatography matrix comprising a dye ligand, wherein the sample is selected from the group consisting of a tissue, a bodily fluid and a culture medium;
    (b) removing contaminants from the dye affinity chromatography matrix;
    (c) eluting the cystine-knot protein from the dye affinity chromatography matrix;
    (d) applying the eluted cystine-knot protein to a reversed-phase chromatography matrix; (e) removing contaminants from the reversed-phase chromatography matrix; and (f) eluting the cystine-knot protein from the reversed-phase chromatography matrix thereby purifying the protein of the cystine-knot superfamily.

2. The method of claim 1, wherein the substantially purified protein of the cystine-knot superfamily is a dimer.

3. The method of claim 1, wherein the protein of the cystine-knot superfamily comprises a platelet-derived growth factor-like protein, a transforming growth factor-beta, a neurotrophin, a glycoprotein hormone, an interleukin, a coagulogen, a mucin, a mucin-like protein or a slit-like protein.

4. The method of claim 3, wherein the platelet-derived growth factor-like protein comprises platelet-derived growth factor, vascular endothelial growth factor, or placenta growth factor-1.

5. The method of claim 3, wherein the transforming growth factor-beta comprises a transforming growth factor-beta, a bone morphogenetic protein, or a growth differentiation factor.

6. The method of claim 3, wherein the neurotrophin comprises brain-derived neurotrophic factor/neurotrophin 3, neurotrophin 4, or beta-nerve growth factor.

7. The method of claim 3, wherein the glycoprotein hormone comprises follitropin, lutropin, thyrotropin or chorionic gonadotropin.

8. The method of claim 3, wherein the mucin-like protein is a bone morphogenetic protein antagonist.

9. The method of claim 1, wherein the dye ligand comprises a triazine dye.

10. The method of claim 1, wherein the sample is of a physiological pH prior to applying the sample to dye affinity chromatography matrix.

11. The method of claim 1, wherein a buffer at physiological pH is used to remove contaminants from the dye affinity chromatography matrix.

12. The method of claim 1, wherein a buffer of a physiological pH and a salt concentration of at least 300 mM is used to elute the cystine-knot protein from the dye affinity chromatography matrix.

13. The method of claim 1, wherein the protein of the cystine-knot superfamily comprises a fusion protein comprising a protein of the cystine-knot superfamily, or fragment thereof, operably linked with a select protein of interest.

14. A method for purifying a select protein of interest comprising:
    (a) obtaining a first sample containing a fusion protein comprising a protein of the cystine-knot superfamily, or fragment thereof, which comprises requisite cysteines necessary to fold into the cystine-knot conformation and binds to an affinity dye ligand, operably linked with a select protein of interest by a protease cleavage site;
    (b) applying said first sample to a dye affinity chromatography matrix comprising a dye ligand so that the cystine-knot protein, or fragment thereof, of the fusion protein binds to the dye affinity chromatography matrix;
    (c) removing contaminants from the dye affinity chromatography matrix; and
    (d) eluting the select protein of interest from the dye affinity chromatography matrix by applying a protease which specifically cleaves the protease cleavage site thereby substantially purifying the select protein of interest.

15. The method of claim 14, further comprising the presteps of
    (a) preparing a fusion protein comprising a protein of the cystine-knot superfamily, or fragment thereof, operably linked with a select protein of interest by a protease cleavage site;
    (b) expressing said fusion protein in a host cell; and
    (c) preparing a first sample from said host cell which contains the fusion protein.

16. The method of claim 14, wherein the dye ligand comprises a triazine dye.

17. The method of claim 14, wherein the sample is of a physiological pH prior to applying the sample to dye affinity chromatography matrix.

18. The method of claim 14, wherein a buffer at physiological pH is used to remove contaminants from the dye affinity chromatography matrix.

19. The method of claim 14, wherein the protein of the cystine-knot superfamily comprises a platelet-derived growth factor-like protein, a transforming growth factor-beta, a neurotrophin, a glycoprotein hormone, an interleukin, a coagulogen, a mucin, or a slit-like protein.

* * * * *

UNITED STATES PATENT AND TRADEMARK OFFICE
CERTIFICATE OF CORRECTION

PATENT NO. : 7,598,356 B2  Page 1 of 1
APPLICATION NO. : 10/887106
DATED : October 6, 2009
INVENTOR(S) : Elliott Bedows et al.

It is certified that error appears in the above-identified patent and that said Letters Patent is hereby corrected as shown below:

Title Page, (*) Notice: Subject to any disclaimer, the term of this patent is extended or adjusted under 35 U.S.C. 154(b) by 340 days.

should read (*) Notice: Subject to any disclaimer, the term of this patent is extended or adjusted under 35 U.S.C. 154(b) by 445 days.

Signed and Sealed this

Twenty-second Day of June, 2010

David J. Kappos
*Director of the United States Patent and Trademark Office*